United States Patent
Dove et al.

(10) Patent No.: US 8,308,362 B2
(45) Date of Patent: Nov. 13, 2012

(54) QUALITY ASSURANCE PHANTOM FOR DIGITAL DENTAL IMAGING AND RELATED METHOD

(75) Inventors: S. Brent Dove, San Antonio, TX (US); Peter Mah, San Antonio, TX (US); W. Doss McDavid, San Antonio, TX (US)

(73) Assignee: Dental Imaging Consultants, LLC, San Antonio, TX (US)

( * ) Notice: Subject to any disclaimer, the term of this patent is extended or adjusted under 35 U.S.C. 154(b) by 219 days.

(21) Appl. No.: 12/913,752

(22) Filed: Oct. 27, 2010

(65) Prior Publication Data
US 2011/0096911 A1 Apr. 28, 2011

Related U.S. Application Data

(60) Provisional application No. 61/255,293, filed on Oct. 27, 2009.

(51) Int. Cl.
G01D 18/00 (2006.01)

(52) U.S. Cl. .......................................... 378/207; 378/204

(58) Field of Classification Search .................... 378/18, 378/38–40, 62, 204, 207
See application file for complete search history.

(56) References Cited

U.S. PATENT DOCUMENTS

| | | | |
|---|---|---|---|
| 4,352,020 A | 9/1982 | Horiba et al. | |
| 4,649,561 A | 3/1987 | Arnold | |
| D340,655 S | 10/1993 | Rao | |
| 5,416,816 A | 5/1995 | Westrup et al. | |
| 5,539,799 A | 7/1996 | Schulze-Ganzlin et al. | |
| 5,544,157 A | 8/1996 | Wenstrup et al. | |
| 5,841,835 A | 11/1998 | Aufrichtig et al. | |
| 6,488,409 B1 | 12/2002 | Vafi et al. | |
| 6,694,047 B1 | 2/2004 | Farrokhnia et al. | |
| 7,056,019 B1 | 6/2006 | Hanson et al. | |
| 7,173,238 B2 | 2/2007 | Karasawa | |
| 7,256,392 B2 | 8/2007 | Sendai et al. | |
| 7,467,892 B2 | 12/2008 | Lang et al. | |
| 7,503,694 B2 | 3/2009 | Gray | |
| 7,775,714 B2 | 8/2010 | Crucs et al. | |
| 2009/0268953 A1 | 10/2009 | Crucs | |
| 2009/0279672 A1 | 11/2009 | Reiner | |
| 2010/0014636 A1 | 1/2010 | Lang et al. | |

OTHER PUBLICATIONS

Mah, P., McDavid, D., Langlais, R.P., Dove, S.B.; "A Comparison of Six Digital Intraoral Radiographic Imaging System;" American Academy of Oral & Maxillofacial Radiology, 57th Annual Session, Kansas City, Missouri; Nov. 15-19, 2006; p. 62. (Abstract). Mah, P., McDavid, D., Langlais, R.P., Dove, S.B.; "A Comparison of Six Digital Intraoral Radiographic Imaging System;" The University of Texas Health Science Center at San Antonio, San Antonio, Texas 78229; Nov. 16, 2009. (Poster).

*Primary Examiner* — Courtney Thomas

(57) ABSTRACT

A quality assurance phantom for intraoral digital dental imaging and related method. The quality assurance phantom measures three different physical properties of an imaging system: dynamic range, contrast detectability, and spatial resolution. The phantom comprises a dynamic range portion having a plurality of steps, each step of the plurality of steps having a different thickness from the other steps; a contrast detail portion having a uniform thickness and a plurality of wells formed therein; a spatial resolution portion having a plurality of line sets, each line set of the plurality of line sets having different line spacing from the other line sets; an attenuating body having uniform thickness positioned between the source and the contrast detail portion and the spatial resolution portion; and a lead mass adjacent to the dynamic range portion.

According to the method of the present invention, a series of images is created and analyzed, either manually or automatically with a computer, to determine a baseline quality assurance exposure (BQAE). At subsequent monitoring intervals therefrom, an image is created using the same exposure parameters as the BQAE and compared to the baseline image to ascertain changes.

17 Claims, 12 Drawing Sheets

Digital Dental Quality Assurance
Initial Baseline Worksheet

Date: _____

Technician: _____

Sensor (Manufacturer, Model, Serial #): _____

X-ray Machine (Manufacturer, Model, Serial #): _____ kVp: _____ mA: _____

Highest Exposure Limit: _____

Lowest Exposure Limit: _____

| Exposure Time | Steps | Line-Pairs | Top Row of Contrast Holes | Second Row of Contrast Holes |
|---|---|---|---|---|
| | | | | |
| | | | | |
| | | | | |
| | | | | |
| | | | | |
| | | | | |
| | | | | |
| | | | | |
| | | | | |
| | | | | |
| | | | | |
| | | | | |
| | | | | |
| | | | | |
| | | | | |
| | | | | |
| | | | | |

Quality Assurance Exposure: _____ sec.

Fig. 9

Longitudinal Quality Assurance Record

Sensor (Manufacturer, Model, Serial #): _____

X-ray Machine (Manufacturer, Model, Serial #): _____ kVp: _____ mA: _____

Baseline Quality Assurance Exposure: _____ sec.

| Baseline Date | Technician | Steps | Line-Pairs | Top Row of Contrast Holes | Second Row of Contrast Holes |
|---|---|---|---|---|---|
| | | | | | |

| Date | Technician | Steps | Line-Pairs | Top Row of Contrast Holes | Second Row of Contrast Holes |
|---|---|---|---|---|---|
| | | | | | |
| | | | | | |
| | | | | | |
| | | | | | |
| | | | | | |
| | | | | | |
| | | | | | |
| | | | | | |
| | | | | | |
| | | | | | |
| | | | | | |
| | | | | | |
| | | | | | |
| | | | | | |
| | | | | | |
| | | | | | |

Fig. 10

QUALITY ASSURANCE PHANTOM FOR DIGITAL DENTAL IMAGING AND RELATED METHOD

CROSS-REFERENCES TO RELATED APPLICATIONS

This application claims the benefit of U.S. provisional application No. 61/255,293, filed Oct. 27, 2009 and entitled "Quality Assurance Phantom for Digital Dental Imaging," which is incorporated by reference herein.

STATEMENT REGARDING FEDERALLY SPONSORED RESEARCH OR DEVELOPMENT

Not applicable.

BACKGROUND OF THE INVENTION

1. Field of the Invention

The present invention relates to intraoral dental imaging. More specifically, the invention is a quality assurance phantom for intraoral digital dental imaging and related method.

2. Description of the Related Art

The degree of servicing dental radiographic equipment varies from office to office and institution to institution. The level of monitoring radiology equipment varies from one jurisdiction to another and range from unknown, annually, every five years, and, in some instances, only when a problem is encountered. As a result, some radiographic imaging systems can be significantly out of tolerance while still in clinical use. The objective of any quality assurance program is to ensure accurate diagnosis and to ensure that doses are kept as low as reasonably achievable (ALARA). This requires a system of regular monitoring procedures to ensure that the various components of the imaging system function within the manufacturer's recommended tolerances.

Most states and regulating bodies have guidelines which state that regular quality assurance of all dental radiographic equipment be performed. Similar guidelines have been advocated by the American Academy of Oral and Maxillofacial Radiology and the American Dental Association. This means regular testing to detect equipment malfunctions, planned monitoring, and scheduled maintenance to produce consistent diagnostic radiographic images. All dental facilities using x-ray equipment, from a simple intraoral dental unit to an advanced three-dimensional imaging system, such as cone beam computed tomography, will benefit from adopting a quality assurance program.

Any intra-oral digital imaging system comprises essentially three components: an x-ray source; a digital image acquisition component (e.g., solid-state sensor or PSP plate and scanner; and an image display component (e.g., a computer or monitor). Each of these components needs to be regularly monitored for performance and function as part of the quality assurance program.

The digital image acquisition component can be evaluated either qualitatively or quantitatively using a radiographic phantom designed to produce a digital image containing information related to fundamental imaging characteristics. These include spatial resolution, contrast resolution or dynamic range, contrast/detail resolution, field uniformity, saturation, and signal to noise response.

One dental radiographic phantom was designed primarily for conventional x-ray film and is commercially available from Fluke Biomedical, formerly Medi-Nuclear Corporation, as the CDRH Dental Image Quality Test Tool. The phantom was developed as a joint collaboration between the Food and Drug Administration (FDA) Center for Devices and Radiological Health (CDRH) and Conference of Radiation Control Program Directors. The phantom consists of a wooden cradle (to hold the test tool body), built-in slots (for attenuation filters), a film slot, an exposure chamber holder, and a mounting screw for use with a tripod. The test tool comes with an aluminum step wedge that is designed for evaluating darkroom fog and consistency testing. The step wedge has two slots: one for exposing a film pack and one for evaluating darkroom fog. The film slot also ensures easy, reproducible placement of the film for consistent imaging. The phantom is designed specifically for testing the functionality of dental x-ray units and provides a means of evaluating half-value layer, determining kVp, and assessing overall image quality, including x-ray film processing. The test tool also contains a human tooth to simulate a clinical image.

A second phantom is the Quart Dental phantom, which is designed to monitor high-contrast and low-contrast special resolution. In addition, a Unfors Mult-O-Meter external detector can be inserted into the phantom to measure kVp, dose and exposure time.

A third phantom is the CD Dent phantom, which is comprised of a three-millimeter aluminum sheet with one hundred cylindrical holes. The CD Dent phantom is designed to optimize the radiation dose and image quality.

A fourth phantom is the DIQUAD analyzer, a hexagonally-shaped device comprising an optically-stimulated light dosimeter to measure dose, and several metal filters and a mesh target to assess image quality.

BRIEF SUMMARY OF THE INVENTION

The present invention is a radiographic phantom and associated method for quality assurance in intraoral digital dental imaging. The quality assurance phantom measures three different physical properties of an imaging system: dynamic range, contrast detectability, and spatial resolution. The phantom comprises a dynamic range portion having a plurality of steps, each step of the plurality of steps having a different thickness from the other steps; a contrast detail portion having a uniform thickness and a plurality of wells formed therein; a spatial resolution portion having a plurality of line sets, each line set of the plurality of line sets having different line widths and line spacing from the other line sets; an attenuating body having uniform thickness positioned between the source and the contrast detail portion and the spatial resolution portion; and a lead mass adjacent to the dynamic range portion.

BRIEF DESCRIPTION OF THE SEVERAL VIEWS OF THE DRAWINGS

FIG. 9 is an initial baseline worksheet that can be used with the method of the present invention.

FIG. 10 is a quality assurance record that can be used with the method of the present invention.

DETAILED DESCRIPTION OF THE INVENTION

Figure 1:
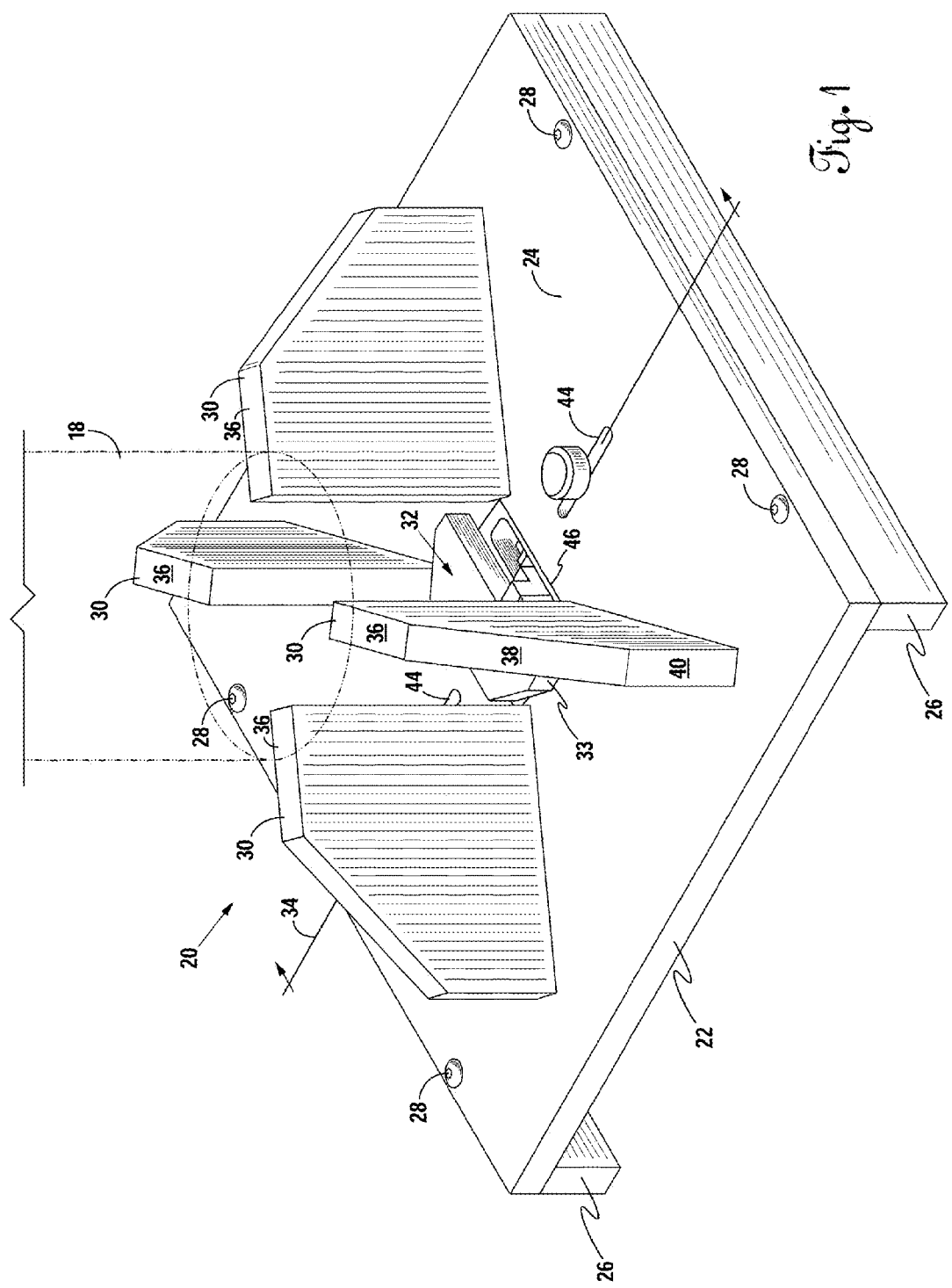
FIG. 1 is an isometric view of a preferred embodiment of the present invention in use with an x-ray source.
Figure 2:
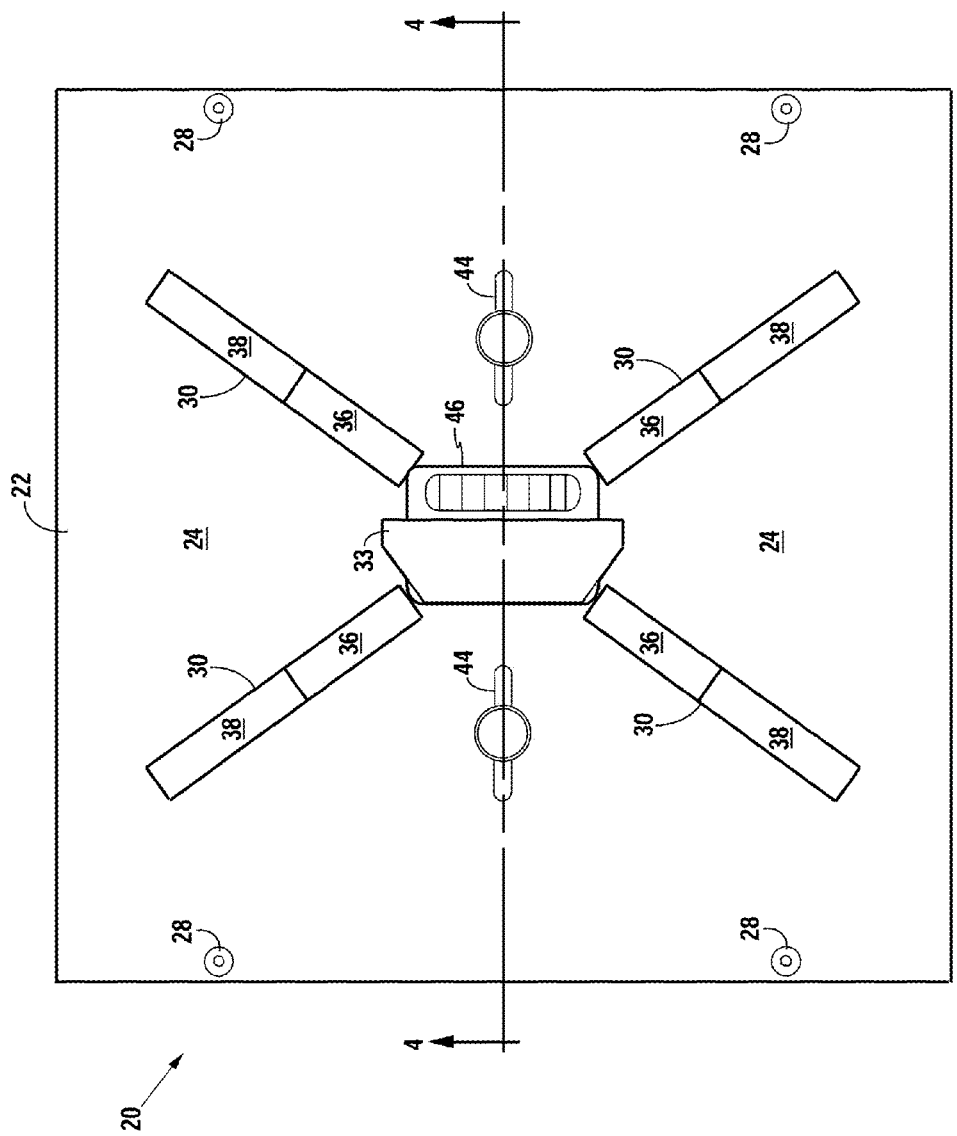
FIG. 2 is a top elevation of the preferred embodiment shown in FIG. 1.

FIGS. 1-4 show a preferred embodiment 20 of the present invention in use with a digital imaging sensor 16 and position indicating device (PID) 18 that is attached to an x-ray source (not shown). Referring to FIGS. 1 & 2, the embodiment 20 comprises a generally-square horizontal acrylic platform 22 having a top surface 24 that is elevated relative to a support surface with acrylic rails 26 positioned at opposing sides of the platform 22. The rails 26 are fastened to the platform 22 using screws 28.

Four acrylic vertical spacing members 30 are fastened to the top surface 24 of the platform 22 and extend vertically from the top surface 24 at right angles. The spacing members 30 are identically shaped and angled relative to the centerline 34 of the platform 22 by approximately fifty degrees. The spacing members 30 are oriented around the center of the platform 22 to define an image acquisition area 32. Each spacing member 30 comprises a horizontal top surface 36, an angled surface 38 relative to the top surface 36, and a vertical surface 40. The PID 18 contacts and rests on the top surfaces 36 of the spacing members 30.

As shown in FIG. 2, longitudinal slots 44 extend through the top platform 22 in line with the centerline 34. An image acquisition assembly 46 is positioned substantially within the image acquisition area 32. An attenuating body 33 of aluminum alloy 1100 is positioned between the PID 18 (FIG. 1) and the image acquisition assembly 46 and fastened to the platform 22.

Figure 3:
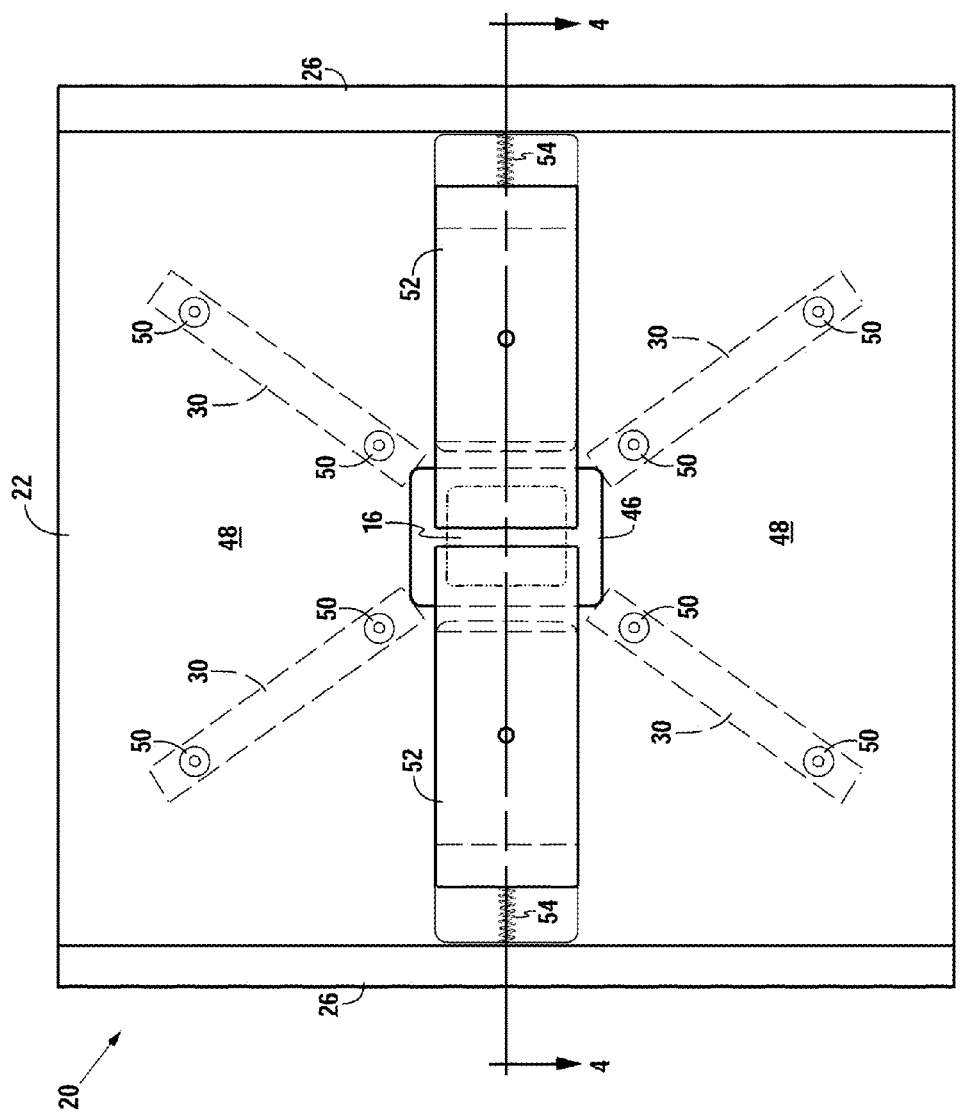
FIG. 3 is a bottom elevation of the preferred embodiment.

FIG. 3 is a bottom elevation of the preferred embodiment showing the bottom surface 48 of the platform 22. Screws 50 fasten the spacing members 30. Two acrylic clamping members 52 are engaged with and hold the sensor 16 stationary relative to the image acquisition assembly 46. The clamping members 52 are urged toward the image acquisition assembly 46 by compression springs 54, which exert an expansive force against the rails 26 and the clamping members 52.

Figure 4:
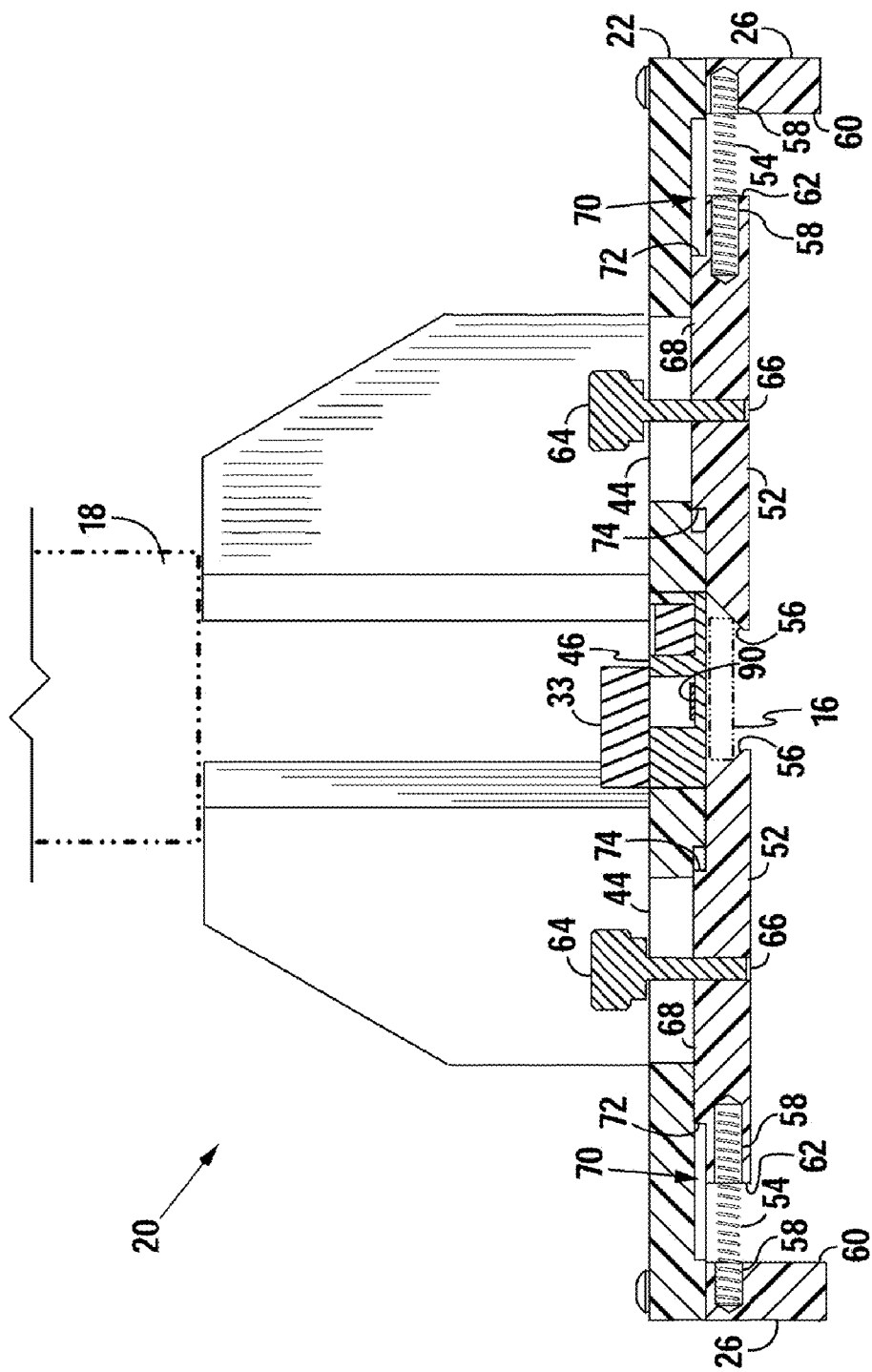
FIG. 4 is a sectional view of the preferred embodiment through line 4-4 of FIG. 2 and FIG. 3.

FIG. 4 is a sectional view through line 4-4 of FIGS. 2 & 3, and more fully shows operation of the clamping members 52. Each clamping member 52 has an angled proximal surface 56 that engages with and holds the sensor 16 in place directly below the image acquisition assembly 46. The distal and proximal ends of the compression spring 54 are positioned in spring holes 58 formed in the proximal sidewalls 60 of the rails 26 and the distal sidewalls 62 of the clamping members 52. As the clamping members 52 are moved closer to the rails 26, the force of the spring 54 increases, urging the clamping members 52 inward.

A knurled thumb screw 64 extends through each of the longitudinal slots 44 in the platform 22 and engages the clamping members 52 through bolt holes 66. Tightening the thumb screws 64 holds the clamping members 52 stationary against the bottom surface 48 of the platform 22, while loosening the screws 64 allows slidable movement of the clamping members 52 toward and away from the image acquisition area 32.

Each clamping member 52 comprises a raised portion 68 fitted within a depression 70 formed in the bottom surface of the platform 22. The raised portions 68 define distal shoulders 72 and proximal shoulders 74. Inward movement of the clamping members 52 is limited by ultimate contact of the proximal shoulder 74 with the proximal sidewall of the depression 70. Lateral movement of the clamping member 52 is limited by ultimate contact with the two lateral surfaces of the depression 70 formed in the bottom surface of the platform 22.

Figure 5:
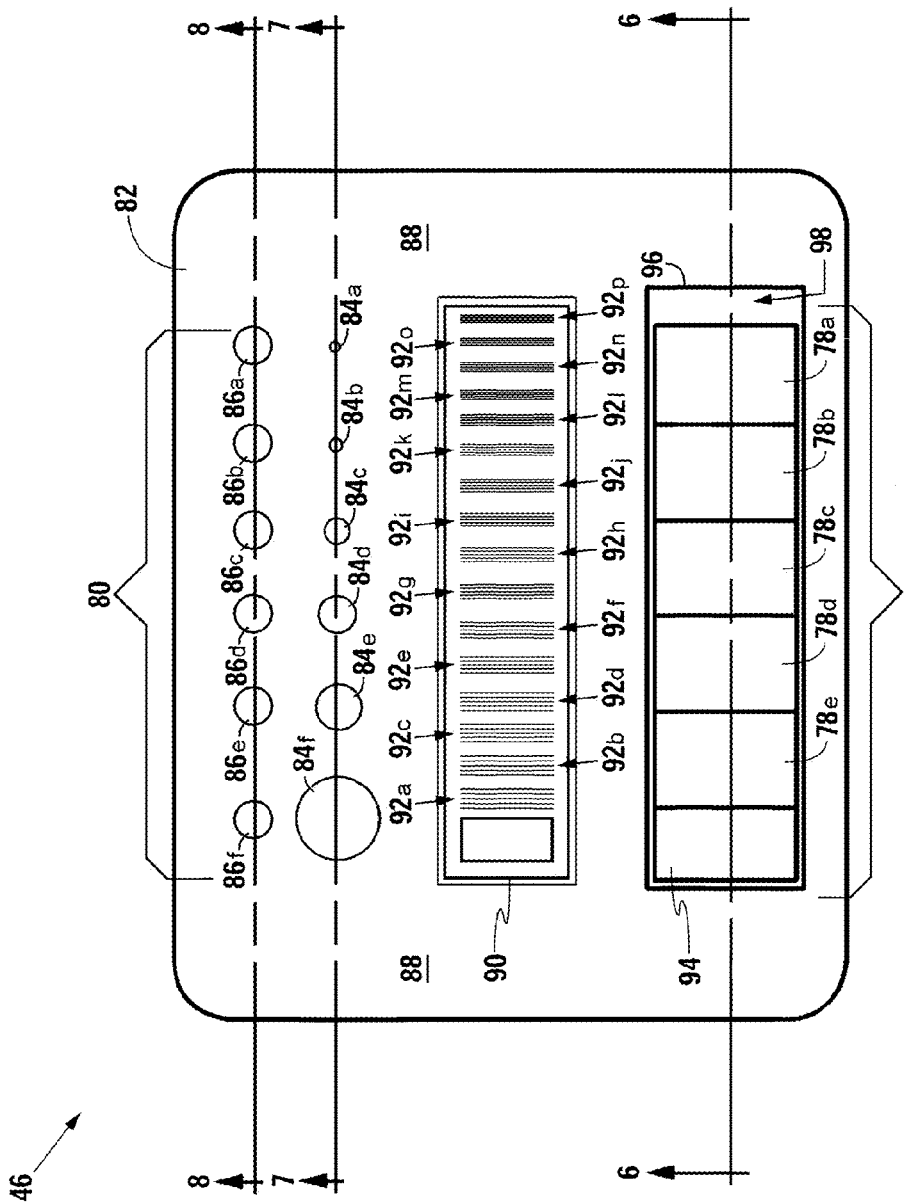
FIG. 5 is a top elevation of the image acquisition assembly of the preferred embodiment.
Figure 6:
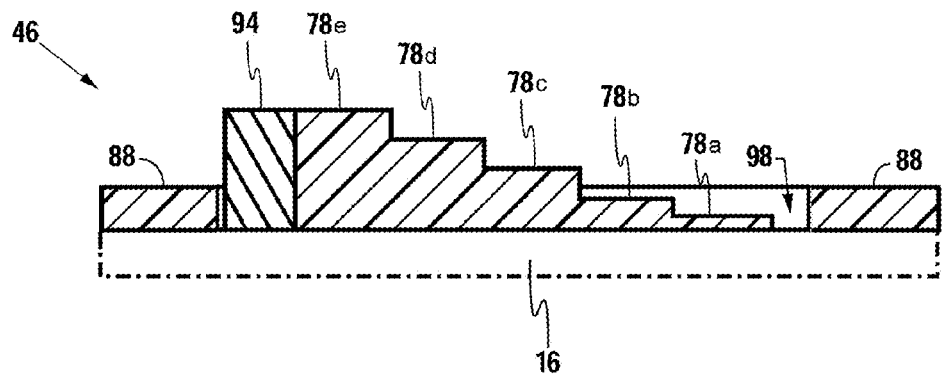
FIG. 6 is a side sectional elevation through line 6-6 of FIG. 5.
Figure 7:
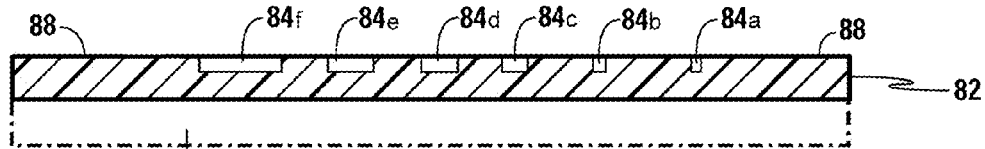
FIG. 7 is a side sectional elevation through line 7-7 of FIG. 5.
Figure 8:
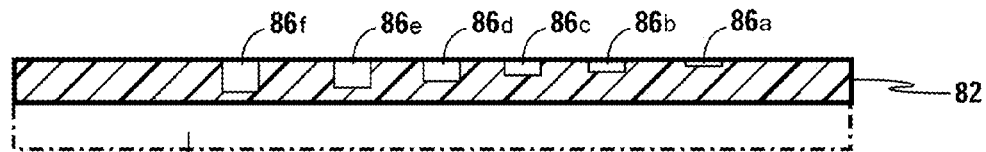
FIG. 8 is a side sectional elevation through line 8-8 of FIG. 5.

FIG. 5 shows a top elevation of the image acquisition assembly 46 of the preferred embodiment 20, which comprises an aluminum dynamic range portion 76 having a plurality of steps 78a-78e of varying thicknesses, a contrast detail portion 80 of a piece 82 of acrylic plastic of uniform thickness with first group 84a-84f and a second group 86a-86f of cylindrical wells formed in the top surface 88 thereof, and a spatial resolution portion 90 having a plurality of high-contrast line sets 92a-92p with gradually increasing spatial frequency encompassing the range of frequencies encountered in dental intra-oral radiography.

The dynamic range portion 76 comprises five steps 78a-78e of varying thickness of aluminum and a lead mass 94 positioned through a cutout 96 formed in the acrylic plastic 82. In the preferred embodiment, the first step 78a is a first thickness; the second step 78b is a second thickness that is greater than the first thickness; the third step 78c is a third thickness that is greater than the second thickness; the fourth step 78d is a fourth thickness that is greater than the third thickness, and the fifth step 24e is a fifth thickness that is greater than the fourth thickness. The steps 78a-78e are integrally formed from a block of aluminum alloy 1100. The dynamic range portion 76 further comprises a lead mass 94 that has a thickness equal to the fifth thickness and is positioned adjacent to the fifth step 78e. Adjacent to the first step 78a is an empty volume 98.

The varying thicknesses of the dynamic range portion 76 cause varying degrees of attenuation of the energy as it propagates from the source, through the image acquisition assembly 46, and to the sensor 16. These varying degrees of attenuation simulate the range of contrast encountered in dental intraoral radiography.

More specifically, energy from the PID 18 is not attenuated as it passes through the empty volume 98. At the other end of the dynamic range portion 76, the lead mass 94 causes complete, or almost complete, attenuation because of the inability of x-rays to propagate through the material. The first through fifth steps 78a-78e cause varying levels of attenuation that are functions of the corresponding thicknesses.

The spatial resolution portion 90 provides for a high-contrast resolution evaluation of the imaging system, and comprises a spatial resolution pattern of sixteen line sets 92a-92p formed of a gold foil on a background. The line sets 92a-92p range from five lines per millimeter for the first line set 92a to twenty lines per millimeter at the sixteenth line set 92p. As the energy from the source propagates through the spatial resolution portion 90, some of the line sets will be discretely discernable while some of the line sets will appear solid, depending on the resolving capabilities of the sensor/source system. The results may be subjectively analyzed with the naked eye or objectively analyzed with image analysis software to remove operator biases such as eyesight, fatigue, viewing conditions, and other factors.

The contrast detail portion 80 provides a low contrast detectability pattern that comprises a first group 84a-84f of six cylindrical wells of identical depth but of varying diameters. In the preferred embodiment, the diameters of the first group of wells range from approximately one-half millimeters to approximately four-and-a-half millimeters. The contrast detail portion 80 also comprises a second group 86a-86f of cylindrical wells, each well having an identical diameter, but varying depths within the second group 86a-86f.

Use of the preferred embodiment is initially described with reference to FIGS. 1-4. The sensor 16 and PID 18 to be analyzed are positioned relative to the embodiment 20. Specifically, the PID 18 is positioned on the horizontal surfaces 36 of the spacing members 30, which provides a fixed, reproducible distance from the image acquisition assembly 46 during each assessment of the quality assurance process, regardless of when the process is performed. In addition, placement of the PID 18 onto the spacing members 30 assures propagation of x-rays normal to the image acquisition area 32.

Referring specifically to FIGS. 3-4, the thumb screws 64 are loosened to allow the clamping members 52 to slide relative to the platform 22. The sensor 16 is placed between the clamping members 52 adjacent to and directly under the image acquisition assembly 46. Angled surfaces 56 of the clamping members 52 contact the sensor 16 to hold it stationary, while the compression springs 54 provide an inward force to immobilize the sensor 16 relative to the embodiment 20. Thereafter, thumb screws 64 may be tightened to prevent inadvertent movement of the sensor 16 as it is maintained against the bottom surface 48 of the platform 22.

When testing multiple sensors of the same design, the invention provides for quick exchange of the sensors by loosening only one of the thumb screws 64, sliding the corresponding clamping member 52 outward to release the sensor 16, inserting the next sensor, and sliding the clamping member 52 inward and retightening the thumbscrew 64. This negates the need to realign the active area of a different sensor of identical make with the image acquisition area and provides for more rapid assessment.

Assessing a sensor/source system with the present invention is a two-step process. First, if the specific sensor/source combination has never been assessed, a technician performs an initial baseline assessment, as will be described infra.

Thereafter, a longitudinal assessment is performed at a predetermined monitoring interval, which may be at a predetermined time-interval or after the occurrence of a particular event (e.g., the sensor is inadvertently dropped or bitten by a patient) that brings operational reliability into question.

To perform an initial baseline assessment, the technician places the sensor directly under the image acquisition assembly 46 and rests the PID 18 on the horizontal surfaces 36 of the spacing members 30. Thereafter, the kVp and mA of the source are adjusted to the settings that will be used for clinical exposures. Starting with the lowest possible exposure time, a series of digital images is acquired and saved at incrementally-increasing exposure times. When exposure times are too short, the resulting images are underexposed, and the different density levels are indistinct in the areas 106, 102e, and 102e of FIG. 11. In contrast, when exposure times are too high, the resulting images are overexposed, and the different density levels are indistinct in the areas of 104, 102a, and 102b of FIG. 11.

Between these two extremes will be a set of images in which all the different density levels will be discernable in the image. The group of images is identified in which all seven density levels—that is, zero density of the empty volume 98, the first through fifth steps 78a-78e of aluminum alloy, and the lead mass 94—are clearly discernable.

Analyzing the set of images, the number of discernable line sets A-P and the number of areas 110a-110f, 112a-112f are determined for each image of the set of images. The lowest exposure time in which the highest line pairs per millimeter and maximum number of wells 110a-110f, 112a-112f can be identified is the Baseline Quality Assurance Exposure (BQAE).

The final step of initial baseline assessment is recording the baseline image as well as the characteristics of the BQAE for future comparison. FIG. 9 discloses an exemplary worksheet that may be used by the technician to record the characteristics of the BQAE.

At each monitoring interval, a longitudinal quality assurance assessment may be performed using a new digital image acquired using the sensor and source settings determined by and recorded during the initial baseline assessment. The image is acquired with the exact same exposure settings as the BQAE.

After the image is acquired, the image can be compared to the baseline image for any change in dynamic range, spatial resolution, and contrast/detail resolution. A change in one or more of these characteristics indicates that corrective action should be taken with respect to the sensor/source system, and alerts the technician that the characteristics of images taken since the BQAE may have changed.

FIG. 10 discloses an exemplary worksheet that may be used by the technician when performing longitudinal quality assessment.

Figure 11:
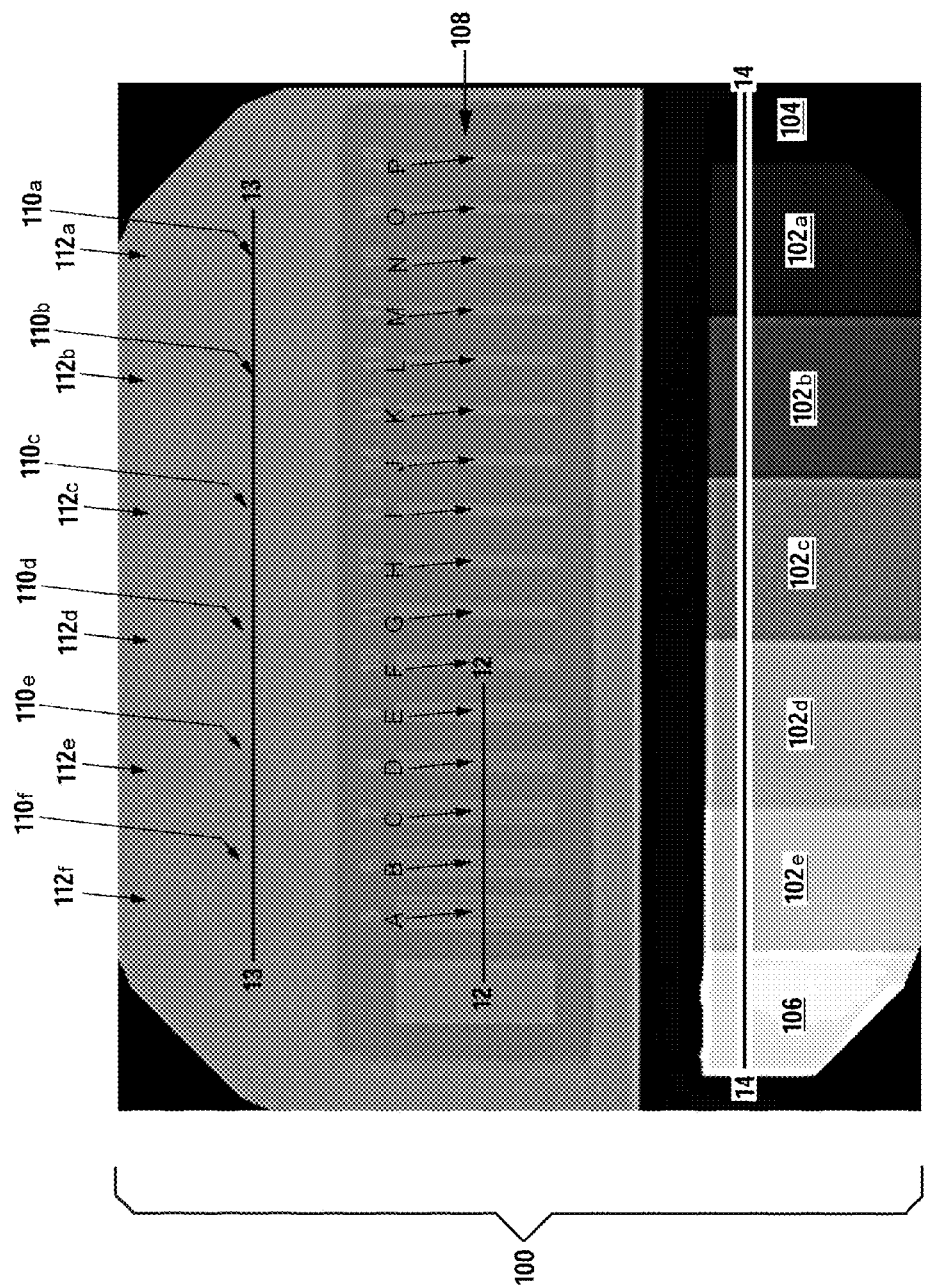
FIG. 11 is an image created using the preferred embodiment of the apparatus.

FIG. 11 is an image 100 created with the preferred embodiment 20 of the invention. The image 100 comprises areas of varying brightness corresponding to exposure to energy from the source, with brighter (i.e., whiter) areas having been exposed to a lesser amount of energy and darker areas having exposed to a greater amount of energy. Specifically, areas 102a-102e correspond to the location of the first through fifth steps 78a-78e of the dynamic range portion 76 in FIG. 5. Area 104 corresponds to the empty volume 98. Area 106 corresponds to the position of the lead mass 94 in FIG. 5. Area 108 corresponds to the spatial resolution portion 90 in FIG. 5. Areas 110a-110f correspond to the positions of the first group of wells 84a-84f. Areas 112a-112f correspond to the positions of the second group of wells 86a-86f in FIG. 5.

Figure 12:
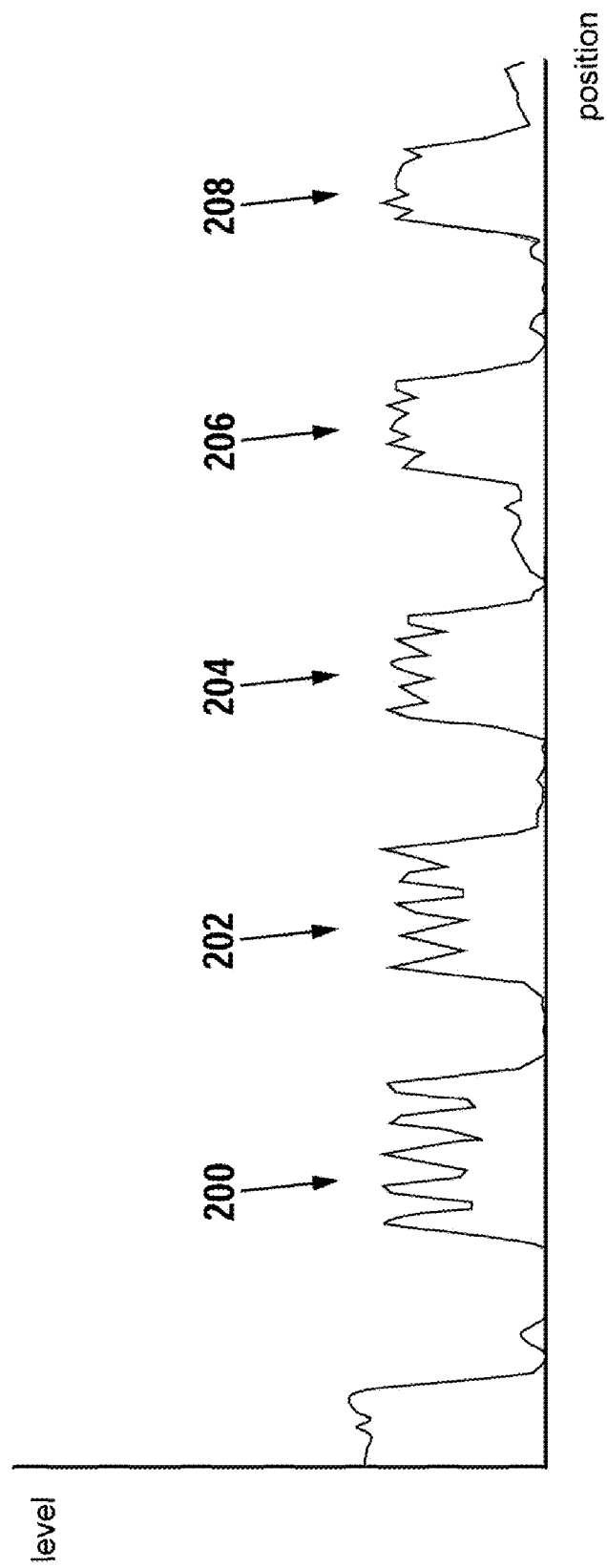
FIG. 12 is exemplary image data showing attenuation of energy propagated through line 12-12 of FIG. 11.

FIG. 12 is a line graph resulting from image analysis of line 12-12 of FIG. 11 plotting position against intensity. Specifically, a first section 200 of the graph corresponds to the energy received at area A of FIG. 11, which has five lines per millimeter; a second section 202 of the graph corresponds to the energy received at area B of FIG. 11, which has six lines per millimeter; a third section 204 of the graph corresponds to the energy received are area C of FIG. 11, which has seven lines per millimeter; a fourth section 206 of the graph corresponds to the energy received at area D of FIG. 11, which has eight lines per millimeter; and a fifth section 208 of the graph corresponds to the energy received at area E of FIG. 11, which has nine lines per millimeter. The greatest number of lines per millimeter that comprises five distinct peaks and four distinct troughs is the line set resolution of that image, which in the present case is the fourth section 206 corresponding to the fourth line set 92d of eight lines per millimeter.

Figure 13:
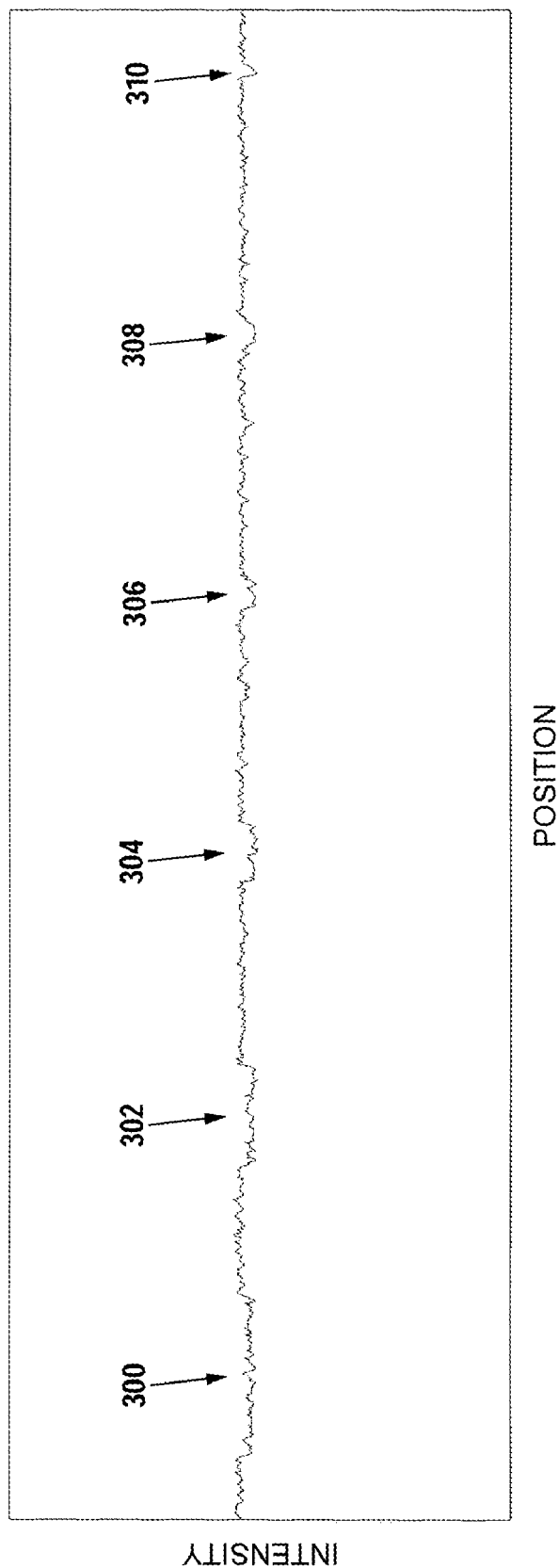
FIG. 13 is exemplary image data showing attenuation of energy propagated through line 13-13 of FIG. 11.

FIG. 13 is an exemplary image data showing attenuation of energy propagated through line 13-13 of FIG. 11. Section 300 corresponds to well 110f. Section 302 corresponds to well 110e. Section 304 corresponds to well 110d. Section 306 corresponds to well 110c. Section 308 corresponds to well 110b. Section 310 corresponds to well 110a.

Figure 14:
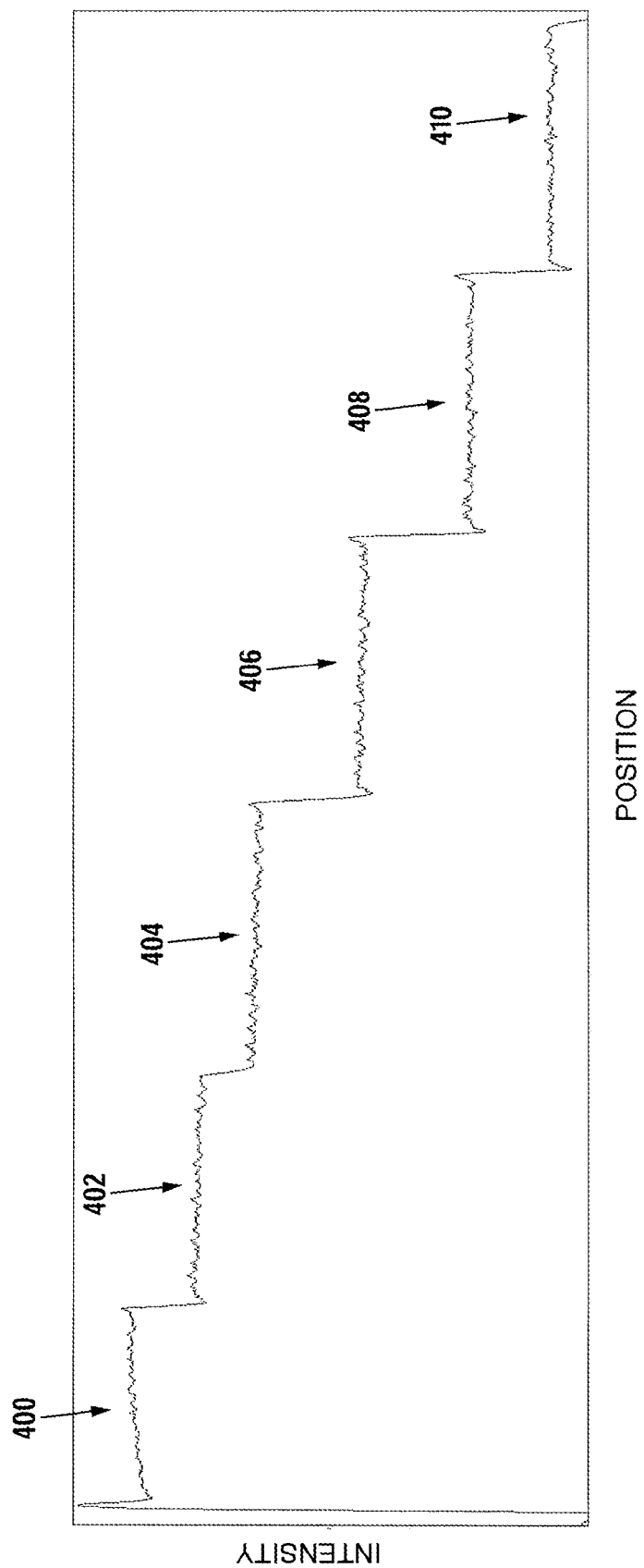
FIG. 14 is exemplary image data showing attenuation of energy propagated through line 14-14 of FIG. 11.

FIG. 14 is an exemplary image data showing attenuation of energy propagated through line 14-14 of FIG. 11. Section 400 corresponds to area 106. Section 402 corresponds to area 102e. Section 404 corresponds to area 102d. Section 406 corresponds to area 102c. Section 408 corresponds to area 102b. Section 410 corresponds to area 102a. Section 412 corresponds to area 104.

The present invention is described in terms of preferred embodiment in which a specific system and method are described. Those skilled in the art will recognize that alternative embodiments of such system, and alternative applications of the method, can be used in carrying out the present invention. Other aspects and advantages of the present invention may be obtained from a study of this disclosure and the drawings, along with the appended claims. Moreover, the recited order of the steps of the method described herein is not meant to limit the order in which those steps may be performed.

We claim:

1. A quality assurance phantom for an intraoral digital dental imaging that maintains clinical source-to-object and object-to-sensor projection geometry, the phantom comprising:
    a horizontal platform having a top surface and a bottom surface;
    a plurality of spacing members extending upwardly from said top surface and defining an image acquisition area, each spacing member of said plurality having a top surface;
    at least two clamping members positioned below said platform, said at least two clamping members moveable toward and away from the image acquisition area;
    at least one attenuating body;
    a dynamic range portion having a plurality of steps, each step of said plurality of steps having a different thickness from the other steps;
    a contrast detail portion having a uniform thickness and a plurality of wells formed therein, said contrast detail portion being located below said at least one attenuating body;
    a spatial resolution portion having a plurality of line sets, each line set of said plurality of line sets having different line spacing from the other line sets, said spatial resolution portion being located below said at least one attenuating body.

2. The phantom of claim 1 wherein said dynamic range portion further comprises a lead mass adjacent to said plurality of steps.

3. The phantom of claim 1 wherein said at least one attenuating body is formed of aluminum alloy 1100.

4. The phantom of claim 1 wherein said plurality of wells comprises a group of cylindrical well, each cylindrical well having an identical depth and a different diameter.

5. The phantom of claim 1 wherein said plurality of wells comprises a group of cylindrical wells, each cylindrical well having an identical diameter and a different depth.

6. The phantom of claim 1 wherein said attenuating portion is an aluminum alloy.

7. The phantom of claim 1 further comprising:
    at least two elevating members attached to the bottom side of said platform;
    at least two springs compressible between the proximal sidewalls of said elevating members and the distal side of said at least two elevating members to urge said clamping members toward said image acquisition area.

8. The phantom of claim 1 further comprising:
    at least two slots formed through said platform between said top surface and said bottom surface;
    at least two thumbscrews extending through said slots and engaged with said at least two clamping members, said thumbscrews moveable within said slots.

9. The phantom of claim 1 wherein said at least two clamping members comprising angled proximal surfaces.

10. The phantom of claim 1 further comprising:
    at least two depressions formed in the bottom surface of said platform, at least two depressions defining proximal and distal shoulders;
    wherein said at least two clamping members comprise a raised portion and inward movement of said clamping member is limited by contact of said raised portion with said proximal shoulders.

11. A method of assuring the quality of a digital dental imaging system over time, the system having an imaging acquisition sensor and an x-ray source, the method comprising the steps of:
    providing a digital imaging phantom comprising:
        a dynamic range portion having a plurality of steps, each step of said plurality of steps having a different thickness from the other steps;
        a contrast detail portion having a uniform thickness and a plurality of wells formed therein, said contrast detail portion being located below an at least one attenuating body;
        a spatial resolution portion having a plurality of line sets, each line set of said plurality of line sets having different line spacing from the other line sets, said spatial resolution portion being located below said at least one attenuating body;
    creating a baseline image, the creating step comprising:
        generating a plurality of images with the sensor and source, each image having a different exposure time;
        selecting a subset of said plurality of images that includes all images of said plurality of digital images in which all density levels of said phantom are discernable;
        selecting a first image from said subset that is the image with the highest exposure time of all images of said subset;
        selecting a baseline image from said subset that is the image with the lowest exposure time that includes the same contrast detail and spatial resolution shown in said first image;
    recording a number of baseline quality assurance exposure, dynamic range, spatial resolution, and contrast resolution of said baseline image.

12. The method of claim 11 further comprising the step of performing a longitudinal quality assurance assessment comprising the steps of:
    adjusting the system settings to the system settings used during creation of the baseline image;
    acquiring a at least one third image using the recorded BQAE;
    comparing the dynamic range, spatial resolution, and contrast resolution of the baseline image to said at least one third image.

13. The method of claim 12 wherein said comparing step comprises the steps of:
    line graphing the energy received by the sensor proximal to the spatial resolution portion of said phantom;
    determining the maximum number of lines per millimeter that shows five distinct peaks and four distinct troughs.

14. The method of claim 13 wherein said determining step is performed by a processor.

15. A quality assurance system for intraoral digital dental imaging having imaging acquisition sensor and an x-ray source, the system comprising: a phantom, comprising:
- a horizontal platform having a top surface and a bottom surface;
- a plurality of spacing members extending upwardly from said top surface and defining an image acquisition area, each spacing member of said plurality having a top surface;
- at least two clamping members positioned below said platform, said at least two clamping members moveable toward and away from the image acquisition area;
- at least one attenuating body;
- a dynamic range portion having a plurality of steps, each step of said plurality of steps having a different thickness from the other steps;
- a contrast detail portion having a uniform thickness and a plurality of wells formed therein, said contrast detail portion being located below said at least one attenuating body;
- a spatial resolution portion having a plurality of line sets, each line set of said plurality of line sets having different line spacing from the other line sets, said spatial resolution portion being located below said at least one attenuating body;
- a processor adapted to receiving digital images acquired by said sensor;
- a computer readable medium electrically connected to said processor, said computer readable medium containing a set of processor readable instructions comprising:
  - generating a plurality of digital images with the sensor and source, each image having a different exposure time;
  - selecting a subset of said plurality of digital images that includes all images of said plurality of digital images in which all density levels of said phantom are discernable;
  - selecting a first image from said subset that is the image with the highest exposure time of all images of said subset;
  - selecting a baseline quality assurance exposure from said subset that is the image with the lowest exposure time that includes the same contrast detail and spatial resolution shown in said first image;
  - recording the number of discernable steps, the number of discernable line sets, and the number of discernable wells of said baseline quality assurance exposure.

16. The quality assurance system of claim 15 wherein said set of instructions further comprises:
- analyzing the representation of energy received by the sensor through the spatial resolution portion of the phantom;
- determining the most dense line set that shows five distinct peaks and four distinct troughs.

17. The quality assurance system of claim 15 wherein said set of instructions further comprises:
- acquiring at least one third image created using the recorded BQAE settings;
- comparing the number of steps, line sets, and wells visible in the baseline image to the at least one third image.

* * * * *